(12) United States Patent
Kaminsky et al.

(10) Patent No.: US 7,825,204 B2
(45) Date of Patent: *Nov. 2, 2010

(54) INORGANIC OXIDE EXTRUDATES

(75) Inventors: Mark P. Kaminsky, Media, PA (US); Edward T. Shawl, Wallingford, PA (US); Steven M. Augustine, Ellicott City, MD (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/641,482

(22) Filed: Dec. 19, 2006

(65) Prior Publication Data

US 2008/0146721 A1    Jun. 19, 2008

(51) Int. Cl.
*C08F 20/06* (2006.01)
*C08F 20/04* (2006.01)

(52) U.S. Cl. .................... 526/317.1; 526/318.3

(58) Field of Classification Search ............. None
See application file for complete search history.

(56) References Cited

U.S. PATENT DOCUMENTS

| | | | |
|---|---|---|---|
| 4,039,474 A | 8/1977 | Feistel et al. | |
| 4,119,474 A | 10/1978 | Whitman et al. | |
| 4,410,501 A | 10/1983 | Taramasso et al. | |
| 4,832,939 A | 5/1989 | Menashi et al. | |
| 4,833,260 A | 5/1989 | Neri et al. | |
| 4,888,319 A | 12/1989 | Daamen et al. | |
| 5,332,710 A | 7/1994 | Nicolau et al. | |
| 5,347,046 A | 9/1994 | White et al. | |
| 5,393,343 A | 2/1995 | Darwin et al. | |
| 5,567,839 A | 10/1996 | Gulliver et al. | |
| 6,022,823 A | 2/2000 | Augustine et al. | |
| 6,034,208 A | 3/2000 | McDaniel et al. | |
| 6,139,623 A | 10/2000 | Darwin et al. | |
| 6,214,958 B1 * | 4/2001 | Le-Khac et al. | 526/318.3 |
| 6,455,711 B1 | 9/2002 | Eller et al. | |
| 6,680,406 B2 | 1/2004 | Harmer et al. | |
| 6,696,596 B1 | 2/2004 | Herzog et al. | |
| 6,706,658 B2 | 3/2004 | White | |
| 6,815,513 B2 * | 11/2004 | Le-Khac et al. | 526/89 |
| 6,821,922 B1 | 11/2004 | Tacke et al. | |
| 6,849,243 B1 | 2/2005 | Hagemeyer et al. | |
| 6,849,570 B2 | 2/2005 | Hasenzahl et al. | |
| 7,074,944 B2 | 7/2006 | Steinbrenner et al. | |
| 2007/0123594 A1 * | 5/2007 | Dogterom et al. | 518/716 |

FOREIGN PATENT DOCUMENTS

| | | | |
|---|---|---|---|
| BE | 1001038 A7 | | 6/1989 |
| EP | 0739868 | * | 10/1996 |
| EP | 1 862 482 A | | 12/2007 |
| JP | 60 122770 A | | 7/1985 |
| JP | 60122770 | * | 7/1985 |
| JP | 60 155567 A | | 8/1985 |
| JP | 07 025665 A | | 1/1995 |
| WO | WO 02/085513 A2 | | 10/2002 |

OTHER PUBLICATIONS

A. Stiles, "Supports Other Than Alumina" in Catalyst Supports and Supported Catalysts, (1987), p. 57.
W. Waddell, "Silica, Amorphous" in Kirk-Othmer Encyclopedia of Chemical Technology, online edition, (2006), John Wiley & Sons, Inc.
T. Egerton, "Titanium Compounds, Inorganic" in Kirk-Othmer Encyclopedia of Chemical Technology, online edition, (2006) p. 12.
J. Vartuli et al., "Potential Applications for M41S Type Mesoporous Molecular Sieves" in Studies in Surface Science and Catalysis: Mesoporous Molecular Sieves, (1998), p. 13.
"Chapter 2, Clay as Potential Catalyst Material" in Zeolite, Clay, and Heteropoly Acid in Organic Reactions, (1992), p. 49.
W. Haag, "Catalysis by Zeolites—Science and Technology" in Zeolites and Related Microporous Materials: State of the Art 1994, (1994) p. 1375.
U. Romano et al., "Selective Oxidation with Ti-Silicalite" in New Developments in Selective Oxidation, (1990), p. 33-38, Elsevier Science Publishers B.V.
R. Szostak, "Non-aluminosilicate Molecular Sieves" in Molecular Sieves: Principles of Synthesis and Identification, (1989), p. 205.
G. Vayssilov, "Structural and Physicochemical Features of Titanium Silicalites" in Catal. Rev.-Sci. Eng., (1997), p. 209, vol. 39(3).
"Particle Size Enlargement" in Handbook of Powder Technology, (1980), p. 112, vol. 1.
*Kirk-Othmer Encyclopedia of Chemical Technology*, Fifth Edition, vol. 25, 2007, pp. 15-21, Wiley-Interscience, A John Wiley & Sons, Inc., Publication.
*Kirk-Othmer Encyclopedia of Chemical Technology*, Fifth Edition, vol. 5, 2007, pp. 598-603, Wiley-Interscience, A John Wiley & Sons, Inc., Publication.
C. Miclea et al., "Microstructure and Properties of Barium Titanate Ceramics Prepared by Mechanochemical Synthesis," *Romanian Journal of Information Science and Technology*, vol. 10, No. 4, 2007, pp. 335-345.
Matthew H. Frey and David A. Payne, "Synthesis and Processing of Barium Titanate Ceramics from Alkoxide Solutions and Monolithic Gels," *Chem. Mater.*, vol. 7, No. 1, 1995, pp. 123-129.

\* cited by examiner

*Primary Examiner*—Karl J Puttlitz
(74) *Attorney, Agent, or Firm*—Yuanzhang Han

(57) ABSTRACT

An extrudate comprising an inorganic oxide and a comb-branched polymer is disclosed. The calcined extrudates are useful catalysts or catalyst supports. A palladium-gold catalyst prepared with a calcined titania extrudate of the invention is useful in making vinyl acetate from ethylene, acetic acid, and oxygen or oxygen-containing gas. A calcined transition metal zeolite extrudate of the invention is used as a catalyst in oxidizing organic compounds with hydrogen peroxide. Incorporation of a comb-branched polymer improves the mechanical properties of inorganic oxide extrudates.

7 Claims, No Drawings

INORGANIC OXIDE EXTRUDATES

FIELD OF THE INVENTION

The invention relates to an extrudate comprising an inorganic oxide and a comb-branched polymer.

BACKGROUND OF THE INVENTION

Inorganic oxide extrudates are useful catalysts or catalyst carriers (Stiles, A. B., "Supports Other Than Alumina," *Catalyst Supports and Supported Catalysts* (1987) Butterworths Publishers, pp. 57-85). Generally an extrusion aid, such as polyether polyols, polyacrylic acids, cellulose, or starch is used to facilitate extrusion and improve the physical and/or mechanical properties of extrudates (see, e.g., U.S. Pat. Nos. 4,039,474, 4,888,319, 4,119,474, and 6,706,658). Despite many efforts, there is a need for new processes to make extrudates with improved physical and/or mechanical properties.

SUMMARY OF THE INVENTION

The invention is an extrudate comprising an inorganic oxide and a comb-branched polymer. The calcined extrudate is useful as a catalyst or catalyst carrier. The invention further includes a process for preparing vinyl acetate comprising reacting ethylene, acetic acid, and oxygen or an oxygen-containing gas in the presence of a palladium-gold catalyst prepared with a calcined titania extrudate. The invention also includes an oxidation process, which comprises reacting an organic compound with hydrogen peroxide in the presence of a calcined transition metal zeolite extrudate. Surprisingly, incorporation of a comb-branched polymer improves the mechanical properties of inorganic oxide extrudates.

DETAILED DESCRIPTION OF THE INVENTION

In one aspect, the present invention is an extrudate comprising an inorganic oxide and a comb-branched polymer. The inorganic oxides are metal oxides, non-metal oxides, mixed oxides, and the like, and mixtures thereof. They include, e.g., silicas, aluminas, titanias, zirconias, magnesias, silica-aluminas, silica-titanias, silica-magnesias, zeolites, clays, and the like, and mixtures thereof. Suitable silicas include, e.g., silica gel, precipitated silica, and fumed silica (see Walter H. Waddell, "Silica, Amorphous," *Kirk-Othmer Encyclopedia of Chemical Technology* online edition, 2006). Suitable titanias can be either rutile, anatase, or a mixture of both phases. Titania may be produced by the chloride process, the sulfate process, the hydrothermal process, or the flame hydrolysis of titanium tetrachloride (see Egerton, T. A., "Titanium Compounds, Inorganic" in *Kirk-Othmer Encyclopedia of Chemical Technology*, online edition, 2006).

Inorganic oxides also include hydrated inorganic oxides (or hydroxides). For example, when an inorganic oxide (e.g., silicon oxide) is formed from an inorganic oxide precursor (e.g., a tetraalkoxysilane), a hydrated inorganic oxide (e.g., hydrated silicon oxide or silicon hydroxide) is formed. Inorganic oxide precursors such as metal hydroxides, alkoxysilanes, alkoxytitanates, alkoxyaluminates, or alkoxyzirconates may be used. They include, e.g., tetraalkoxysilanes, tetraalkoxytitaniums, tetraalkoxyzirconiums, trialkoxyaluminiums. These precursors are converted to inorganic oxides or hydrated inorganic oxides (or hydroxides) during the formation of the extrudate.

Suitable inorganic oxides include mesoporous molecular sieves such as MCM-41, MCM-48; see Vartuli, J. C., et al., "Potential Applications for M41S Type Mesoporous Molecular Sieves," in *Studies in Surface Science and Catalysis: Mesoporous Molecular Sieves* (1998) Elsevier Science B.V. pp. 1375-94.

Suitable clays can be found in "Chapter 2. Clay as Potential Catalyst Material," *Zeolite, Clay, and Heteropoly Acid in Organic Reactions* (1992) Kodansha Ltd., Tokyo, pp. 49-98.

Zeolites are microporous crystalline solids with well-defined structures. Generally they contain one or more of Si, Ge, Al, B, P, or the like, in addition to oxygen. Many zeolites occur naturally as minerals and are extensively mined in many parts of the world. Others are synthetic and are made commercially for specific uses. Zeolites have the ability to act as catalysts for chemical reactions that take place mostly within their internal cavities. Acidic zeolite catalysts are used in many organic reactions, including cracking, isomerization, and alkylation; see W. O. Haag, "Catalysis by Zeolites-Science and Technology," in *Zeolites and Related Microporous Materials: State of Art 1994* (1994) Elsevier Science B.V. pp. 13-22.

Transition metal zeolites (zeolites comprising transition metals in their frameworks) are useful catalysts for many organic transformations, such as oxidation reactions (see *New Developments in Selective Oxidation*, pp. 33-38). A transition metal is a Group 3-12 element. The first row of them are from Sc to Zn. Preferred transition metals are Ti, V, Mn, Fe, Co, Cr, Zr, Nb, Mo, and W. When the transition metal zeolite is used for an oxidation reaction, particularly preferred are Ti, V, Mo, and W. Most preferred is Ti. Preferred titanium zeolites are titanium silicates (titanosilicates). Preferably, they contain no element other than titanium, silicon, and oxygen in the lattice framework (see R. Szostak, "Non-aluminosilicate Molecular Sieves," in *Molecular Sieves: Principles of Synthesis and Identification* (1989) Van Nostrand Reinhold, pp. 205-82). Small amounts of impurities, e.g., boron, iron, aluminum, sodium, phosphorous, copper, and the like, and mixtures thereof, may be present in the lattice. The amount of impurities is preferably less than 0.5 wt. %, more preferably less than 0.1 wt. %. Preferred titanium silicates generally have a composition corresponding to the following empirical formula: $xTiO_2 \cdot (1-x)SiO_2$, where x is between 0.0001 and 0.5000. More preferably, the value of x is from 0.01 to 0.125. The molar ratio of Si:Ti in the lattice framework of the zeolite is advantageously from 9.5:1 to 99:1, most preferably from 9.5:1 to 60:1. Particularly preferred titanium zeolites are titanium silicalites (see *Catal. Rev.-Sci. Eng.*, 39(3) (1997) 209). Examples of these include TS-1 (titanium silicalite-1, a titanium silicalite having an MFI topology analogous to that of the ZSM-5 aluminosilicate), TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, and ZSM-12 are also suitable for use. The most preferred is TS-1.

A zeolite is generally prepared in the presence of an organic templating agent (see, e.g., U.S. Pat. No. 6,849,570). Suitable templating agents include alkyl amines, quaternary ammonium compounds, etc. When a zeolite is crystallized, it usually contains the organic templating agent within its crystal structure. A zeolite containing a templating agent may be used in the present invention. Preferably, a template-free zeolite is used.

When the extrudate comprises a mixture of two or more inorganic oxides, one or more oxides may serve as a binder. Binders are well known in the art. For example, in a zeolite-silica extrudate, the zeolite may act as the active component of the catalyst and the silica binds and strengthens the extrudate.

The extrudate comprises a comb-branched polymer. A comb-branched polymer comprises a polymer backbone, a carboxylic side-chain, and a polyether side-chain. The carboxylic side-chain may comprise a carboxylic acid, a carboxylate salt, or mixtures of both. The preferred carboxylic side chain is a carboxylic acid group (—COOH).

The polyether side-chain is preferably represented by

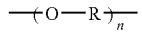

wherein n is from 3 to 500, more preferably from 10 to 250, and R is an organic moiety containing a carbon atom linked to the oxygen through a single covalent bond. The polyether may contain two or more different repeating units containing different R moieties. R may be an aromatic group or an aliphatic group. Saturated aliphatic groups are preferred. Particularly preferred are alkylene groups such as ethylene, propylene, 1,4-butylene, isopropylene, or isobutylene; most preferred are ethylene and propylene. The preferred polyethers are accordingly polyoxyalkylene, e.g., polyoxyethylene, polyoxypropylene, and oxypropylene/oxyethylene copolymers.

The polyether side-chain may be attached to the backbone of the comb-branched polymer by any suitable chemical linkage. The linkage may be an ester, amide, imide, ether, amine, or thioether functionality, or a carbon-carbon bond. Preferably, the polyether side-chains are attached to the polymer backbone through an ester, amide, or imide functionality, as in the comb-branched polymer prepared by polymerizing acrylic acid and a polyether acrylate macromonomer (see U.S. Pat. No. 6,034,208) and in the polymer prepared by grafting a polyether amine to a poly(acrylic acid) (see, e.g., U.S. Pat. No. 5,393,343).

The molar ratio of carboxylic side-chains to polyether side-chains in the comb-branched polymer is not critical. Typically, the molar ratio is in the range of 1:1 to 200:1. Preferably, the ratio is in the range of 2:1 to 50:1.

Preferred comb-branched polymers comprise recurring units of ethylenic carboxylic monomer and a polyether macromonomer. An ethylenic carboxylic monomer comprises a carbon-carbon double bond and a carboxylic group such as a carboxylic acid, a carboxylate salt, or a carboxylic anhydride. Suitable ethylenic carboxylic monomer contains from 3 to 10 carbon atoms. Examples include acrylic acid, methacrylic acid, crotonic acid, vinylacetic acid, 4-pentenoic acid, maleic acid, maleic anhydride, itaconic acid, mesaconic acid, fumaric acid, citraconic acid, and mixtures thereof. Preferably, the ethylenic carboxylic monomer is acrylic, e.g., acrylic acid, methacrylic acid, maleic acid, maleic anhydride, fumaric acid, and mixtures thereof. More preferably, it is acrylic acid, methacrylic acid, or a mixture of both.

Suitable polyether macromonomers have a polyether chain and a carbon-carbon double bond, which can be either at the end of or within the polyether chain. Examples include polyether monoacrylates, polyether monomethacrylates, polyether monoallyl ethers, polyether monomaleates, and polyether monofumarates. The polyether portion of the macromonomer can be an alkylene oxide polymer having a number average molecular weight (Mn) within the range of about 500 to about 10,000. Suitable alkylene oxides include ethylene oxide, propylene oxide, 1,2-butylene oxides, and the like, and mixtures thereof. The polyether macromonomers preferably have from 0 to 5 hydroxy groups. The polyether macromonomer can be a linear or a branched polymer, a homopolymer or a copolymer, and a random or a block copolymer.

Examples of polyether macromonomers are poly(propylene glycol) acrylates or methacrylates, poly(ethylene glycol) acrylates or methacrylates, poly(1,4-butylene glycol) acrylates or methacrylates, poly(ethylene glycol) methyl ether acrylates or methacrylates, acrylates or methacrylates of an oxyethylene and oxypropylene block or random copolymer, poly(propylene glycol) allyl ethers, poly(ethylene glycol) allyl ethers, poly(propylene glycol) monomaleates, and the like, and mixtures thereof. Preferred polyether macromonomers are poly(propylene glycol) acrylates or methacrylates, poly(ethylene glycol) acrylates or methacrylates, and acrylates or methacrylates of an oxyethylene and oxypropylene copolymer. More preferred are acrylates or methacrylates of an oxyethylene/oxypropylene copolymer.

The polyether macromonomer can be prepared by the oxyalkylation of an olefinic substrate containing a hydroxy or carboxylic acid group with one or more alkylene oxides in the presence of a catalyst as described in U.S. Pat. No. 6,034,208, the teachings of which are incorporated herein by reference. In another example, poly(1,4-butylene glycol) allyl ether is prepared by polymerization of tetrahydrofuran in the presence of allyl alcohol and a base catalyst such as potassium hydroxide or sodium hydroxide. A solid base catalyst may also be used (see, e.g., U.S. Pat. Nos. 6,680,406, 6,455,711, and 7,074,944).

The ratio of ethylenic carboxylic monomer to polyether macromonomer is generally within the range from 1:99 to 99:1 by weight. The preferred range is from 5:95 to 75:25.

Many methods can be used to prepare the comb-branched polymer. One method involves the copolymerizing an ethylenic carboxylic monomer and a polyether macromonomer (see U.S. Pat. Nos. 6,034,208 and 6,815,513). Preferably, the monomer is acrylic. More preferably, the monomer is acrylic acid, methacrylic acid, or a mixture of both.

When a comb-branched polymer is prepared by copolymerization of an ethylenic carboxylic monomer and a polyether macromonomer, other comonomers may be copolymerized. The comonomers include olefins, vinyl aromatics, vinyl halides, vinyl ethers, vinyl esters, vinyl pyrrolidones, conjugated dienes, unsaturated sulfonic acids, unsaturated phosphonic acids, and the like, and mixtures thereof. The amount of comonomer used is generally <50 wt. %, preferably <20 wt. % of the total amount of monomers. Methods for preparing comb-branched polymers are described in U.S. Pat. Nos. 6,214,958 and 6,815,513, the teachings of which are incorporated herein by reference.

Another suitable method for preparing the comb-branched polymer is to react a carboxylic polymer with a polyether amine. A carboxylic polymer is a polymer that comprises carboxylic side-chains, including carboxylic acids, carboxylate salts, and carboxylic anhydrides. Examples of carboxylic polymers are homo or copolymers of ethylenic carboxylic monomers, e.g., acrylic, methacrylic, maleic, fumaric, citraconic, itaconic acids, or dicarboxylic acid monoesters. Homo or copolymers of acrylic acid or methacrylic acid are preferred. The carboxylic polymer may contain units derived from other ethylenic monomers, such as styrene, alpha-methylstyrene, sulfonated styrene, maleic acid, acrylonitrile, butadiene, and the like. Such other ethylenic monomer derived units, when present, can be up to 20 wt. %, preferably, up to 10 wt. % of the total polymer.

Polyether amines are used to graft the carboxylic polymer to form the desired comb-branched polymer. A polyether amine comprises an amine group within the polymer backbone or as an end group. The methods of making comb-branched polymers by grafting a polyether amine to a carboxylic polymer are disclosed in U.S. Pat. Nos. 5,393,343 and 6,139,623, the teachings of which are herein incorporated by reference.

To make an extrudate, the inorganic oxide and the comb-branched polymer are typically mixed using any suitable method, such as mulling or kneading. The operation is generally carried out at a temperature in the range of 10 to 150° C., preferably at room temperature. The mulling or kneading may be performed under any pressure, preferably at 0.1-10 atmospheric pressure. Typically, it lasts for 1 min to 10 h.

The mixture is usually made into a stiff dough for extrusion. If necessary, a solvent may be added to the mixture. Suitable solvents include water, alcohols, ethers, esters, amides, aromatic solvents, halogenated solvents, and the like, and mixtures thereof. Preferred solvents are water and alcohols. Water is the most preferred.

The extrudates of the invention are made by extrusion, a manufacturing process in which a material is pushed through a die or an orifice to create long objects of a fixed cross-section. Extrusion is commonly used to process plastics or food, and to form adsorbents or catalysts. Any conventional extruder may be used. The extrudate usually has a diameter of 0.5 to 10 mm, in particular from 1 to 5 mm. A suitable screw-type extruder is described in "Particle Size Enlargement," *Handbook of Powder Technology*, vol. 1 (1980) pp. 112-22.

The comb-branched polymer serves as an extrusion aid. An extrusion aid helps the mixing, mulling, and extruding operation, and may improve the mechanical and/or physical properties of the extrudate such as crushing strength, surface area, pore size, or pore volume. For example, an extrusion aid may promote bridging of inorganic particles during the kneading, molding, drying, and calcination, and/or ensure the mechanical stability of the extrudate during extrusion and calcination. The extrusion aid can also help disperse solvent more homogeneously throughout the paste. Extrusion aids are usually removed during calcination. When a metal carboxylate is used as an extrusion aid, the metal (e.g., its oxide) is generally incorporated into the extrudate during calcination.

The extrudate may comprise other extrusion aids, including, e.g., alkyl amines, carboxylic acids, alkyl ammonium compounds, amino alcohols, cellulose, cellulose ethers, starch, polyacrylates, polymethacrylates, poly(vinyl alcohol)s, poly(vinylpyrrolidone)s, poly(amino acid)s, polyethers, poly(tetrahydrofuran)s, metal carboxylates, and the like, and mixtures thereof. Examples of cellulose ethers include sodium carboxymethylcellulose, hydroxyethylcellulose, methylcellulose, and derivatives thereof. Preferred poly(alkylene oxide)s are poly(ethylene oxide)s, poly(propylene oxide)s, or copolymers of ethylene oxide and propylene oxide (see U.S. Pat. No. 6,706,658).

The extrudate produced comprises at least 10 wt. %, preferably at least 20 wt. %, more preferably at least 30 wt. % inorganic oxide, and at least 0.1 wt. % comb-branched polymer.

The extrudate may be dried. The drying operation removes at least a portion of solvents (e.g., water, alcohols) from the extrudate. The drying may be performed at 10 to 200° C. at atmospheric pressure or under vacuum. The drying may occur in air or an inert atmosphere.

The extrudate may be calcined to produce a calcined extrudate. Preferably, the calcination is carried out in an oxygen-containing atmosphere to burn off the organic materials (e.g., residual solvent, extrusion aids, templating agent) contained in the extrudate. The calcination may be carried out at 400 to 1000° C., more preferably from 450 to 700° C. Sometimes, it is beneficial to initially calcine the extrudate in an inert atmosphere (e.g., nitrogen, helium) to thermally decompose the organic compounds contained in the extrudate, and then burn off the organic materials in an oxygen-containing atmosphere. Generally, a calcined extrudate after the calcination contains <0.5 wt. % carbon. Preferably, it contains <0.1 wt. % carbon.

The invention includes a process for preparing vinyl acetate. The process comprises reacting ethylene, acetic acid, and oxygen or an oxygen-containing gas in the presence of a palladium-gold catalyst comprising palladium-gold supported on a calcined titania extrudate of the invention.

The palladium-gold catalyst is generally prepared by impregnation techniques. Typically, a calcined titania extrudate is simultaneously or, as is more often the case, successively treated with aqueous solutions of palladium and gold salts. The concentrations and the amounts of solutions used depend on the desired concentrations of palladium and gold in the final catalyst. Water is then removed leaving the palladium and gold salts deposited on the extrudate. Representative palladium and gold salts include palladium chloride, sodium chloropalladite, palladium nitrate, palladium sulfate, auric chloride, tetrachloroauric acid, sodium tetrachloroaurate, and the like. Solutions of tetrachloroauric acid and palladium chloride or sodium chloropalladite are most commonly used in view of their high water solubility and ready availability.

The palladium-gold catalyst may comprise an alkali metal. An alkali metal compound may be added in the solutions of the palladium and/or gold salts. Alternatively, the impregnation of titania extrudate with the palladium and gold solutions is carried out before treatment with the aqueous solution of the alkali metal compound. The preferred alkali metal is potassium.

The calcination of the impregnated titania extrudate is carried out at a temperature in the range of 100° C. to 600° C. in an inert or oxidizing gas such as helium, nitrogen, argon, neon, nitrogen oxides, oxygen, air, carbon dioxide, and the like. Mixtures of the aforementioned gases may also be used. In a highly useful embodiment of the invention, the calcination is carried out in nitrogen, oxygen or air, or mixtures thereof. Calcination times can vary but generally are between 0.5 and 5 h.

Following the calcination step, the resulting product is chemically reduced to convert at least a portion of the palladium and gold salts to the corresponding metals. In general, any known procedure using conventional reducing agents such as ammonia, carbon monoxide, hydrogen, hydrocarbons, olefins, aldehydes, alcohols, hydrazine, primary amines, carboxylic acids, carboxylic acid salts, and carboxylic acid esters can be used. Hydrogen, ethylene, propylene, alkaline hydrazine, and alkaline formaldehyde are highly useful reducing agents; and ethylene and hydrogen are particularly preferred. While pure hydrogen may be used, it is more common to utilize a mixture of hydrogen and an inert gas such as nitrogen, helium, argon, or the like. These mixtures generally contain up to about 50 volume percent (vol. %) hydrogen and, more typically, are comprised of about 5 to 25 vol. % hydrogen and 75 to 95 vol. % inert gas. Reduction times typically vary from 1 to 5 h. Temperatures employed for the reduction can range from 20 to 600° C.

The palladium-gold catalyst produced by the process of the invention generally contains from 0.05 to 3 wt. % palladium and from 0.05 to 3 wt. % gold. More preferably, the catalyst contains from 0.5 to 1.5 wt. % palladium and from 0.25 to 0.75 wt. % gold.

The preparation methods of supported palladium-gold catalysts described in U.S. Pat. Nos. 5,332,710, 5,347,046, 5,567,839, 6,022,823, 6,696,596, and 6,849,243, the disclosures of which are incorporated herein by reference, are applicable for the present palladium-gold catalysts.

Typically, the vinyl acetate is prepared by passing acetic acid, ethylene, and oxygen or oxygen-containing gases at temperatures of from 100 to 220° C., preferably from 120 to 200° C., and pressures of from 0.1 to 2.5 MPa, preferably from 0.1 to 2 MPa, over the palladium-gold catalyst. Unreacted components can be recycled. In some cases, dilution with inert gases such as nitrogen or carbon dioxide is also advantageous. Carbon dioxide is particularly suitable for dilution in a circulation mode of operation because it is usually formed during the reaction.

The invention also includes an oxidation process comprising reacting an organic compound and hydrogen peroxide in the presence of a calcined transition metal zeolite extrudate of the invention.

Suitable and preferred transition metal zeolite extrudates and their preparation methods discussed in the previous sections apply in the present process.

A variety of organic compounds may be oxidized. Examples include olefins, alkanes, arenes, alcohols, aldehydes, ketones, thioethers, and the like.

In one preferred oxidation process, the organic compound is an olefin, and the oxidation product is an epoxide. Suitable olefins include any olefin having at least one carbon-carbon double bond and generally from 2 to 60 carbon atoms. Preferably, the olefin is an acyclic alkene containing 2 to 30 carbon atoms. In a particularly preferred process, the olefin is propylene and the epoxide is propylene oxide.

Alkane oxidation to alcohols, ketones, or other oxygenated products is another preferred oxidation process of the invention. The process is valuable because the oxygenated products are usually more valuable than nonfunctionalized hydrocarbons. Suitable alkanes include those containing halogen, oxygen, aryl groups, and the like, and mixtures thereof. Examples include ethane, propane, n-butane, isobutane, toluene, ethylbenzene, and cumene.

Other oxidation reactions include, e.g., oxidations of arenes to phenols, phenols to catechols, ketones to esters or lactones, thioethers to sulfoxide and/or sulfones, ammoximation of aldehydes or ketones in the presence of ammonia or an amine to make oximes (e.g., the conversion of cyclohexanone to cyclohexanone oxime).

The oxidation step may be performed using a continuous flow, semi-batch, or batch mode. Preferably, the oxidation is performed in a continuous fixed-bed or a plurality of separate fixed-beds. It is advantageous to work at a pressure of 1-200 bars and at a temperature in the range of 0-250° C., more preferably, 20-200° C.

The oxidation process may use a solvent. Suitable solvents are liquid under the reaction conditions. They include, for example, oxygen-containing hydrocarbons such as alcohols, aromatic and aliphatic solvents such as toluene and hexane, chlorinated aromatic and aliphatic solvents such as chlorobenzene and methylene chloride, nitriles such as acetonitrile, carbon dioxide, and water. Suitable oxygenated solvents include alcohols, ethers, esters, ketones, carbon dioxide, water, and the like, and mixtures thereof. Preferred oxygenated solvents include water and lower aliphatic $C_1$-$C_4$ alcohols such as methanol, ethanol, isopropanol, and tert-butanol, and mixtures thereof. Fluorinated alcohols can be used.

It may be advantageous to use a buffer in the oxidation step. The buffer may typically be added to the solvent to form a buffer solution, or to the hydrogen peroxide solution. The buffer may also be added directly to the oxidation reaction mixture. The buffer is employed in the reaction to improve the reaction rate and/or selectivities. Buffers useful in this invention include any suitable salts of oxyacids, the nature and proportions of which in the mixture are such that the pH of their solutions may preferably range from 3 to 10, more preferably from 4 to 9, and most preferably from 5 to 8. Suitable salts of oxyacids contain an anion and cation. The anion may include phosphate, carbonate, bicarbonate, sulfate, carboxylates (e.g., acetate), borate, hydroxide, silicate, aluminosilicate, and the like. The cation may include ammonium, alkylammonium (e.g., tetraalkylammoniums, pyridiniums, and the like), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of buffer in the solvent is from 0.0001 M to 1 M, preferably from 0.0005 M to 0.3 M. The buffer useful in this invention may include ammonium hydroxide which can be formed by adding ammonia gas to the reaction system. For instance, one may use a pH=12-14 solution of ammonium hydroxide to balance the pH of the reaction system. More preferred buffers include alkali metal phosphate, ammonium phosphate, and ammonium hydroxide.

The following examples merely illustrate the invention. Those skilled in the art will recognize many variations that are within the spirit of the invention and scope of the claims.

EXAMPLE 1

Comb-Branched Polymer A

The reaction is carried out in a 1-L reaction kettle equipped with a stirrer, a temperature controller, a heating device, a nitrogen purge device and a product outlet. The outlet tube is set so that the reactor holds about 320 mL of material. There are three inlet addition pumps, one for the mixture of monomers in water, one for the initiator, and one for the chain-transfer agent. The product outlet tube leads into a second reactor which is equipped with a stirrer, a temperature controller, a heating device and a nitrogen purge device. The second reactor is sized to collect all product produced after the reaction has reached steady state. The first reactor is charged with 50 mL of water to cover the stirrer and the reactor is then purged with nitrogen for about 20 min. A mixture of a methacrylate of an oxyethylene/oxypropylene random copolymer having an oxyethylene/oxypropylene ratio of 70:30 by weight and Mn of about 5,000 (2,070 g, 0.414 mol), methacrylic acid (99.9 g, 1.16 mol) and water (1719 g) are charged to the monomer feed tank. An aqueous ammonium persulfate solution (1.25 wt. %) is charged to the initiator feed reservoir and an aqueous 3-mercaptopropionic acid solution (2.2 wt. %) is charged to the chain transfer agent feed reservoir. The reactor is heated to 65° C. and then the feed pumps are started with a feed rate of 262 g/h for the monomer feed, 29 mL/h for the initiator feed, and 19 mL/h for the chain-transfer agent feed. The reaction temperature is maintained at 65° C. and the reactor is under continuous nitrogen purge. The reactor effluent is diverted until the reaction has reached a steady state and then the product is collected in the second reactor for about 40 min. Thereafter, the second reactor is heated for 3 h at 65° C. to complete the reaction. The product collected is designated as Polymer A.

EXAMPLE 2

Comb-Branched Polymer B

The reaction is carried out as described in Example 1. A mixture of a methacrylate of an oxyethylene/oxypropylene random copolymer having an oxyethylene/oxypropylene ratio of 70:30 by weight and a number average molecular weight of about 3,000 (900 g, 0.3 mol), acrylic acid (136 g, 1.83 mol), and water (610 g) is charged to the monomer feed tank. The reactor is heated to 65° C. under a continuous nitrogen purge. The feed pumps are started with a feed rate of 150 g/h for the monomer feed, 28.5 mL/h for the initiator feed, and 30.5 mL/h for the chain transfer agent feed. The reactor effluent is diverted until the reaction has reached a steady state and then the product is collected in the second reactor for about 1 h. At the end of the period the second reactor is heated for another 3 h to complete the reaction. The product is designated as Polymer B (MW 45,000).

A sample of Polymer B is titrated with an aqueous ammonium hydroxide solution to obtain a sample designated as Polymer B-1 with pH=2.8. Polymer B-1 contains 43 wt. % solid.

EXAMPLE 3

Comb-Branched Polymer C

The reaction is carried out as described in Example 1. A mixture of a methacrylate of an oxyethylene/oxypropylene random copolymer having an oxyethylene/oxypropylene ratio of 70:30 by weight and a number average molecular weight of about 3,000 (1,800 g, 0.6 mol), methacrylic acid (146 g, 1.7 mol), and water (1,495 g) is charged to the monomer feed tank. Water (50 mL) is charged to the reactor. The reactor is heated to 65° C. and then the feed pumps are started with a feed rate of 370 g/h for the monomer feed, 41.8 mL/h for the initiator feed, and 36 mL/h for the chain transfer agent feed. The reaction temperature is maintained at 65° C. and the reactor is under continuous nitrogen purge. The reactor effluent is diverted until the reaction has reached a steady state and then the product is collected in the second reactor for about 12 h. At the end of that period it is heated for another 3 h in the second reactor to complete the reaction. The product collected is treated with dilute caustic solution to give 40 wt. % solids and a pH of 4. The final product is designated Polymer C.

EXAMPLE 4

Titania Extrudates Prepared with Polymer A

Titania powder (DT51, Millennium Chemicals, 400 g), carboxymethylcellulose (8.2 g), Polymer A prepared in Example 1 (5.5 g solids), water (217 g), and concentrated ammonium hydroxide (14.8 M, 16 g) are combined. The loose mixture is transferred to a Thermo Haake Rheomix 3000 mixer (625 mL internal volume) and kneaded using sigma shaped blades for 30 min. The blades are turned in a counter-rotating fashion at 50 rotations per minute (rpm) by a Thermo Haake Rheocord 300p drive unit. The drive unit measures the torque necessary to maintain blade rpm, and this value is integrated as a function of time to determine the total energy consumed over 30 min.

The paste is removed from the mixing bowl and aged in a sealed plastic bag for 24 h. The paste is then extruded into ⅛" cylinders using a Thermo Haake Rheomex 202p motorized with a Rheocord 300p drive unit. The extrudates are dried in air at room temperature for 24 h, then at 105° C. for 16 h. Then the extrudates are calcined in air. The calciner temperature is raised from room temperature to 500° C. at a ramp rate of 1° C./min, held at 500° C. for 1 h, then ramped from 500° C. to 700° C. at 10° C./min rate, and finally held at 700° C. for 6 h before cooling down.

Some physical properties of the calcined titania extrudates are listed in Table 1. The crush strength of the calcined titania extrudates is measured with a Chatillon crush strength analyzer (Model DPP 50). The force necessary for failure in 25 measurements is averaged to give the reported value. Bulk density is measured by placing 40 g of extrudates in a 100-mL graduated cylinder (1" nominal outer diameter). The graduated cylinder is tapped until the apparent volume no longer changes, and then this value is divided into the mass to calculate bulk volume. Voidage is determined by adding the pellets to 50 mL water in a second graduated cylinder and then tapping until all voids are filled. The resulting water level is subtracted from the total volume of the water and the pellets taken separately to determine the void volume occupied by water. Total pore volume is determined by pouring the mixture through a sieve basket, shaking to remove excess water and then weighing the wet extrudates. The increase in mass over the initial 40 g of extrudates divided by the density of water is taken as the measure of the pore volume.

EXAMPLE 5

Titania Extrudates Prepared with Polymer B

The procedure of Example 4 is repeated, except that Polymer B prepared in Example 2 (5.5 g solids) is used instead of Polymer A.

EXAMPLE 6

Titania Extrudates Prepared with Polymer C

The procedure of Example 4 is repeated, except that Polymer C prepared in Example 3 (5.5 g solids) is used instead of Polymer A.

COMPARATIVE EXAMPLE 7

Titania Extrudates Prepared with Poly(Ethylene Oxide)

The procedure of Example 4 is repeated, except that poly(ethylene oxide) (Alpha Aesar, M.W.=100,000, 5.5 g) is used instead of Polymer A.

TABLE 1

Preparation and Properties of Titania Extrudates

|  | Example | | | |
| --- | --- | --- | --- | --- |
|  | 4 | 5 | 6 | Comp. 7 |
| Extrusion aid | Polymer A | Polymer B | Polymer C | Poly(ethylene oxide) |
| Total mixing energy (KJ) | 42.6 | 42.7 | 44.3 | 48.4 |
| Crush strength (lbs) | 31.88 | 32.98 | 36.96 | 36.88 |

TABLE 1-continued

Preparation and Properties of Titania Extrudates

| | Example | | | |
|---|---|---|---|---|
| | 4 | 5 | 6 | Comp. 7 |
| Bulk density (g/ml) | 1.03 | 0.88 | 0.96 | 1.1 |
| Voidage (%) | 67.9 | 71.4 | 70.0 | 67.9 |
| Pore volume (mL/g) | 30.1 | 32.5 | 19.9 | 26.8 |

EXAMPLE 8

Au/Pd-on-Titania (Catalyst D)

$NaAuCl_4$ (0.987 g), $Na_2PdCl_4$ (2.645 g), and $NaHCO_3$ (2.760 g) are dissolved in water (24 mL). The solution is applied to titania extrudates prepared in Example 4 (100 g) using a disposable pipette while the extrudates are tumbled in a rotating dish until all of the available extrudate pore volume is filled. The impregnated extrudates are allowed to tumble for another 30 min, and then dried at 80-85° C. for 1 h using a hot air gun. The extrudates are further dried in an oven in air at 105° C. for 16 h, then exhaustively washed with warm deionized water using a Soxhlet extractor to remove chloride.

The above extrudates are heated in a 1.5" nominal O.D. tube reactor at 210° C. in flowing air (flow rate, 200 mL/min) at 70 psig for 3 h. After the reactor is purged with nitrogen, a gas mixture (20 vol. % hydrogen in nitrogen) is introduced into the reactor (500 mL/min) at 70 psig. The temperature is ramped to 500° C. at a rate of 10° C./min, and held at 500° C. for 3 h. The reactor is purged with nitrogen and the resultant catalyst is cooled to room temperature under nitrogen flow.

The extrudates (25 g) are contacted with an aqueous solution containing 5 wt. % potassium acetate and 0.5 wt. % potassium hydroxide (50 mL) at room temperature for 10 min. The mixture is decanted, and the treated catalyst is dried at 105° C. in an oven in air for 4 h. Catalyst D is obtained.

EXAMPLES 9-11

Au/Pd-on-Titania (Catalysts E, F, G)

The procedure of Example 8 is repeated, except that the extrudates prepared in Examples 5, 6, 7 are used.

EXAMPLES 12-14

Catalyst Testing

Catalysts D, E, and F are evaluated for vinyl acetate production in a fixed-bed reactor (stainless steel, nominal 1 inch O.D.). The bed volume is 30 mL, and the catalyst is mixed with inert alpha alumina cylindrical pellets (⅛" in diameter, surface area 4 $m^2$/g, pore volume 0.25 mL/g) in a weight ratio of 2.5:1 alumina to catalyst. The feed contains 84.7 wt. % ethylene, 9.9 wt. % acetic acid, 3.8 wt. % oxygen, and 1.6 wt. % nitrogen. The reactor pressure is 80 psig and the space velocity relative to catalyst bed is 3,800/h at standard temperature and pressure. The reactor is cooled using a fluidized sand bath, the temperature of which is set at 130° C. The product stream is analyzed by gas chromatography (GC). Oxygen conversion, selectivity, and yield for vinyl acetate after 100 h on stream are calculated from the GC results and listed in Table 2. Oxygen conversion is calculated by dividing the amount of oxygen consumed by the total amount of oxygen fed to the reactor. Oxygen selectivity is the amount of oxygen consumed in making vinyl acetate divided by total oxygen consumed. Oxygen yield is the product of oxygen conversion multiplied by oxygen selectivity.

The results in Table 2 show the effect of the extrusion aid on catalyst performance.

TABLE 2

Catalyst Performance in Vinyl Acetate Formation

| | Example | | |
|---|---|---|---|
| | 12 | 13 | 14 |
| Catalyst | D | E | F |
| Extrusion aid | Polymer A | Polymer B | Polymer C |
| Oxygen conversion (%) | 44.5 | 33.4 | 39.5 |
| Oxygen selectivity (%) | 77.4 | 76.6 | 74.6 |
| Oxygen yield (%) | 34.4 | 25.6 | 29.5 |

EXAMPLES 15-17

Titania Extrudates and Catalysts

Extrudates are prepared using three different concentrations of Polymer A (prepared in Example 1) according to the procedure described in Example 4 except that sodium carboxymethylcellulose and benzyl alcohol are used instead of carboxymethylcellulose as extrusion aids (Table 3). Catalysts G, H, and I are prepared with the calcined extrudates according to the procedure of Example 8. Catalysts G, H, and I are evaluated according to the procedure of Examples 12-14. Test results are shown in Table 3.

TABLE 3

Extrudate Preparation and Catalyst Performance

| | Example | | |
|---|---|---|---|
| | 15 | 16 | 17 |
| Extrudate preparation | | | |
| Titania (wt. %) | 61.8 | 61.1 | 60.4 |
| Water (wt. %) | 33.1 | 32.7 | 32.4 |
| Polymer A (wt. %) | 0.8 | 2.0 | 3.0 |
| Carboxymethylcellulose, sodium salt (wt. %) | 1.3 | 1.3 | 1.2 |
| Benzyl alcohol (wt. %) | 0.5 | 0.5 | 0.5 |
| Ammonium hydroxide (wt. %) | 1.9 | 1.8 | 1.8 |
| Catalyst performance | | | |
| Catalyst | G | H | I |
| Oxygen conversion (%) | 32.0 | 46.2 | 20.9 |
| Oxygen selectivity (%) | 80.0 | 75.4 | 73.8 |
| Oxygen yield (%) | 25.7 | 34.8 | 15.4 |

EXAMPLE 18

Catalyst Testing

Catalyst D is tested by following the procedure described in Examples 12-14, except that the sand bath temperature is set at 135° C. instead of 130° C. Test results are shown in Table 4.

COMPARATIVE EXAMPLE 19

Catalyst Testing

Catalyst G is tested by following the procedure described in Example 18. Test results are shown in Table 4.

Comparison of Examples 18 and 19 indicates that Catalyst D (prepared from extrudates produced with Polymer A as an extrusion aid) gives better performance than Catalyst G (produced with poly(ethylene oxide) as an extrusion aid).

TABLE 4

Catalyst Performance in Vinyl Acetate Formation

| | Example | |
|---|---|---|
| | 18 | Comp. 19 |
| Catalyst | D | G |
| Extrusion aid | Polymer A | Poly(ethylene oxide) |
| Oxygen conversion (%) | 51.8 | 50.6 |
| Oxygen selectivity (%) | 74.2 | 70.8 |
| Oxygen yield (%) | 38.4 | 35.8 |

EXAMPLE 20

TS-1 Extrudate (Catalyst J)

Titanium silicalite-1 (TS-1) samples are prepared by following procedures disclosed in U.S. Pat. Nos. 4,410,501 and 4,833,260. The samples and calcined in air at 550° C.

TS-1 (60 g), carboxymethylcellulose sodium salt (Sigma-Aldrich, 2.72 g), and polyethylene oxide (PEO) powder (0.88 g) are mixed in a plastic beaker. This mixture is added to a Brabender Prep-Mixer muller (450 mL) with Sigma blades in a 3:2 rotational configuration. The muller is motorized by a C.W. Brabender Prep-Center Motor Drive unit (Model DT-51 with a 5 HP motor). After the mixture is mulled at 20-30 rpm for 10 min, Polymer B-1 (17.1 g) is added and mixed for 5 min. A Ludox silica sol (AS-40, Aldrich, 40.18 g) is added to the paste at 30 rpm. Then distilled, deionized (DIUF) water (11.1 g) is added at 40 rpm mixing speed. It is mulled for another 5 min. The paste is transferred to a plastic bag to be aged overnight.

The aged paste is extruded using a Brabender single screw, ¾", 10:1 extruder fitted with a ¹/₁₆" single die. The paste is added to the feed hopper and pushed into the screw with a Teflon rod. The extrusion is operated at 10 rpm at 23° C. The pressure in the extruder head is at about 50-150 psig. The extrudates are collected in a glass tray. After being dried in air for 18 h, the extrudates are calcined in air in a muffle furnace at 550° C. for 8 h (temperature ramp rate 2-5° C./min). The extrudate catalyst (Catalyst J) contains 1.5 wt. % Ti, 0.17 wt. % Na, and <100 ppm Al. The nitrogen BET surface area is 340 m$^2$/g. Pellet crush strength is 2.36 lbs. The crush strength is measured by using Chatillon-Antek DFS Digital Force Gauge, fitted with flat platens on an MT test stand using an average of 10 extrudates that ranges in length from 5 to 8 mm. The DFS gauge is set in the "Break Detect" Mode which stores the maximum force (in lbs) exerted before the extrudate breaks. The force exerted for total extrudate crush is recorded as described in ASTM D 4179-01.

EXAMPLE 21

Epoxidation of Propylene

TS-1 extrudate (Catalyst J) prepared in Example 20 may be tested by the following procedure. Catalyst J (10 g) is packed in a SS tube reactor (½" ID). A solution containing 15 wt. % hydrogen peroxide in a methanol/water solvent (3/1 weight ratio) containing 100 ppm ammonium hydroxide is continuously flowed through the catalyst bed at a weight hourly space velocity of 0.54/h (grams of hydrogen peroxide per gram catalyst per hour). At a reactor pressure of about 300 psig, propylene is fed with the hydrogen peroxide solution to the reactor such that the propylene in the liquid phase is about 30 wt. %. Temperature of the reactor is maintained at 60-65° C. Propylene oxide selectivity is expected to be 85-90% at hydrogen peroxide conversion of 95-99%. Propylene oxide selectivity is the moles of propylene oxide formed as a percentage of the moles of hydrogen peroxide consumed. Small amounts of propylene glycol methyl ethers and propylene glycol are expected to form as byproducts.

We claim:

1. An extrudate comprising and a comb-branched polymer comprising a polymer backbone, a carboxylic side-chain, and a polyether side-chain, wherein the titania constitutes at least 10 weight percent, and the comb-branched polymer constitutes at least 1 weight percent of the extrudate.

2. The extrudate of claim 1 wherein the comb-branched polymer comprises recurring units of ethylenic carboxylic monomer and a polyether macromonomer.

3. The extrudate of claim 2 wherein the ethylenic carboxylic monomer is an acrylic monomer.

4. The extrudate of claim 2 wherein the ethylenic carboxylic monomer is selected from the group consisting of acrylic acid, methacrylic acid, and mixtures thereof.

5. A calcined extrudate of claim 1.

6. The calcined extrudate of claim 5 wherein the calcination is performed in the presence of an oxygen-containing gas.

7. The calcined extrudate of claim 5 wherein the calcination is performed at a temperature of 450 to 700° C.

* * * * *